(12) United States Patent
Chen

(10) Patent No.: US 7,195,867 B2
(45) Date of Patent: *Mar. 27, 2007

(54) METHOD FOR DETECTION OF MULTIPLE TEST MATERIALS IN A SAMPLE

(75) Inventor: Hai Xing Chen, Toronto (CA)

(73) Assignee: ACGT Medico Inc., Toronto (CA)

( * ) Notice: Subject to any disclaimer, the term of this patent is extended or adjusted under 35 U.S.C. 154(b) by 76 days.

This patent is subject to a terminal disclaimer.

(21) Appl. No.: 10/035,861

(22) Filed: Dec. 26, 2001

(65) Prior Publication Data

US 2002/0061535 A1    May 23, 2002

Related U.S. Application Data

(63) Continuation-in-part of application No. 09/326,297, filed on Jun. 4, 1999, now Pat. No. 6,337,214, which is a continuation-in-part of application No. 09/093,532, filed on Jun. 8, 1998, now Pat. No. 6,174,733.

(51) Int. Cl.
*C12Q 1/68* (2006.01)
*C07H 21/04* (2006.01)

(52) U.S. Cl. ............... 435/6; 536/24.31; 536/24.32

(58) Field of Classification Search ............ 435/6, 435/7.1, 91.1, 91.2, 287.2; 536/24.3–24.33, 536/23.1, 22; 436/578

See application file for complete search history.

(56) References Cited

U.S. PATENT DOCUMENTS

| | | | | |
|---|---|---|---|---|
| 5,175,209 A | * | 12/1992 | Beattie et al. ............ | 525/54.11 |
| 5,447,837 A | * | 9/1995 | Urnovitz .................... | 435/5 |
| 5,672,475 A | * | 9/1997 | Lee et al. .................. | 435/6 |
| 5,804,384 A | * | 9/1998 | Muller et al. .............. | 435/6 |
| 5,876,918 A | * | 3/1999 | Wainwright et al. ....... | 435/4 |
| 5,945,249 A | * | 8/1999 | Patel et al. ................ | 430/200 |
| 6,174,733 B1 | * | 1/2001 | Chen ......................... | 436/501 |
| 6,261,771 B1 | * | 7/2001 | Bohannon .................. | 435/6 |
| 6,297,006 B1 | * | 10/2001 | Drmanac et al. .......... | 435/6 |
| 6,337,214 B1 | * | 1/2002 | Chen ......................... | 436/501 |
| 6,714,733 B2 | * | 3/2004 | Kobayashi ................ | 396/133 |

* cited by examiner

*Primary Examiner*—Suryaprabha Chunduru

(57) ABSTRACT

A method for sequentially detecting multiple target nucleic acid fragments in a sample includes steps of adding a sample into a column having a test snare which has thereon multiple single strand capture DNA sequences; wherein each capture sequence binds specifically with one target nucleic acid fragment, and forms a double strand segment; washing out unbound target nucleic acid fragment; adding a first DNA probe, which has thereon a chemical label, to attach specifically to a probe binding site of the first target nucleic acid fragment; washing out unbound first probe; adding a triggering solution to trigger the chemical label; and detecting signals on the test snare for determining the first target nucleic acid fragment; subsequently, adding a second DNA probe to bind specifically to the second target nucleic acid fragment; washing, triggering and detecting signals for determining the second target nucleic acid fragment in the same manner.

13 Claims, 10 Drawing Sheets

METHOD FOR DETECTION OF MULTIPLE TEST MATERIALS IN A SAMPLE

CROSS REFERENCE TO RELATED APPLICATION

This application is a continuation-in-part of patent application Ser. No. 09/326,297 filed Jun. 4, 1999, now issued as U.S. Pat. No. 6,337,214, which is a continuation-in-part of patent application Ser. No. 09/093,532 filed Jun. 8, 1998, now issued as U.S. Pat. No. 6,174,733. All prior applications are herein incorporated by reference in their entirety.

FIELD OF THE INVENTION

The present invention relates to a method and apparatus for the detection of multiple test materials in a test sample. In particular, the method relates to a sequential detection of multiple nucleic acid fragments, such as DNAs or RNAs, in a test sample.

BACKGROUND OF THE INVENTION

Historically, the diagnosis of diseases has depended upon clinical manifestations. However, new techniques of detecting diseases have been developed with the advent of monoclonal antibody and nucleic acid detection methods. The detection of nucleic acid has been used for diseases associated with abnormal gene products, such as anemia, Huntington's disease and certain thalassemia mutations. In addition, the detection of nucleic acid has been used for bacterial and viral diseases, such as Human Immunodeficiency Virus (HIV). Moreover, nucleic acid detection methods have been applied to detect water and food contaminations, such as *E. coli* contamination.

As appreciated by those skilled in the art, the detection of a pathogen indicator has applicability to the detection of certain diseases associated with abnormal genes, certain diseases associated with the presence of an identifiable nucleic acid sequence and certain diseases associated with the immune system. The pathogen indicator described herein includes DNA, RNA, antibody, antigen, and other proteins.

Known manual pathogen indicator detection methods in research and clinical laboratories tend to have low accuracy, low sensitivity and are subject to human error, both in carrying out the methods and in interpreting the results. Other methods, e.g. culturing methods, are not suitable for many diseases. For example, tuberculosis has a very slow growth rate, which makes detection difficult or even not possible. Most of the previous tests are demanding of time, skill and concentration. So much so, that in many jurisdictions the number of tests that can be conducted by one technician is limited by regulation. This serves to raise the cost of testing, as it is so labor dependent.

On the other hand, in many clinical tests, multiple test materials, such as multiple nucleic acid fragments, in a test sample need to be detected for proper diagnosis of a disease, or for identifying proper cause of a clinical condition. Sometimes, a multiple target analysis not only confirms the presence of certain microorganism, but also identifies the species of the organism, which is important for determination of proper treatments. For example, in the case of determining *E. Coli* contamination of water or food, at least three genes need to be detected in a sample, wherein positive results in at least two genes confirm the presence of the bacteria. Currently, the multiple test material detections are performed separately. It is known that a small amount of bacteria *E. Coli* can cause diseases. Therefore, dividing available sample, particularly when it is limited, for three separate tests reduces accuracy of the detections and the detection limits.

U.S. Pat. No. 5,804,384 to Muller et al. discloses devices that each include a vessel or a channel containing a linear array of binding elements, each having a binding factor, or probe, specific for a distinct target analyte. The devices can be used in methods for the simultaneous analysis of multiple analytes in a sample. Muller et al. teach that because detected analytes are physically separated on the devices, it is not necessary to use distinct labels on the detector probes that are specific for different analytes.

U.S. Pat. No. 5,876,918 to Wainwright et al. discloses a preactivated chromatography tip having multi-layered receptor elements. In a typical format of three layers of receptor, one layer is for the target analyte, and two layers are for positive and negative controls which contain pre-bound positive and negative controls, respectively. The receptor elements, including controls, are designed specifically for a single analyte for which the detection is sought. This method and device are not suitable for multiple target material analysis. Furthermore, the prebound controls do not reflect analyte binding and other reaction conditions that the target material experiences.

For all the above reasons, a new method and apparatus for detecting multiple test materials, particularly multiple nucleic acid fragments, in a sample with a true inline control is desirable, which is accurate, less costly, and is sensitive to determining if there is an error in the method.

SUMMARY OF THE INVENTION

In one embodiment, the present invention provides a method for detecting multiple test materials in a test sample using a test column. The method comprises the steps of: (a) adding a test sample into a test column, the test column having at least a test snare having thereon at least two target capture materials, a first target capture material being specific to a first test material in the test sample and a second target capture material being specific to a second test material in the test sample; wherein the first test material binds to the first target capture material to form a bound first test material and the second test material binds to the second target capture material to form a bound second test material; (b) washing the test column to remove unbound test materials; (c) adding a first probe to attach specifically to the bound first test material, the first probe having thereon a first chemical label; (d) washing the test column to remove unbound first probe; (e) detecting signals generated by the first chemical label on the test snare for determining the presence of the first test material; (f) adding a second probe to attach specifically to the bound second test material, the second probe having thereon a second chemical label; (g) washing the test column to remove unbound second probe; and (h) detecting signals generated by the second chemical label on the test snare for determining the presence of the second test material. The method further comprises the steps of adding a first triggering solution to trigger the first chemical label prior to detecting signals in step (e); washing the test column to remove the first triggering solution prior to adding the second probe in step (f); and adding a second triggering solution to trigger the second chemical label prior to detecting signals in step (h).

In a further embodiment, the method further comprises adding at least two positive controls into the test column in step (a), the test column further comprising a positive control snare which is separate spatially from the test snare by an intervening air space, the positive control snare having thereon a positive control capture material; and wherein the first positive control and the second positive control bind to the positive control capture material to form a bound first positive control and a bound second positive control; wherein in step (c) the first probe further attaches to the bound first positive control and the second probe further attaches to the bound second positive control; wherein step (e) further comprises detecting signals generated by the first chemical label on the positive control snare for determining the presence of the first positive control; and step (h) further comprises detecting signals generated by the second chemical label on the positive control snare for determining the presence of the second positive control.

Moreover, the method further comprises adding a negative control into the test column in step (a), the test column further comprising a negative control snare which is separate spatially from other snares by an intervening air space, the negative control snare having thereon a negative control capture material which is specific to the negative control; and wherein the negative control binds to the negative control capture material to form a bound negative control; and wherein step (e) and (h) further comprise detecting signals generated on the negative control snare.

Additionally, the method further comprises a detection of background signals of the test sample on a blank snare of the test column; the blank snare being separate spatially from other snares by an intervening air space and having thereon no capture materials.

In another embodiment, the present invention provides a method for detecting multiple target nucleic acid fragments, such DNA, RNA, and PNA, in a test sample. The method comprises the steps of: (a) adding a test sample containing single strand target nucleic acid fragments into a test column, the test column having at least a test snare having thereon at least two single strand target capture DNA sequences, a first target capture DNA sequence being specific to a first target nucleic acid fragment in the test sample and a second target capture DNA sequence being specific to a second target nucleic acid fragment in the test sample; wherein the first target nucleic acid fragment binds to the first target capture DNA sequence by forming a double strand target nucleic acid segment at a capture binding site of the first target nucleic acid fragment, and the second target nucleic acid fragment binds to the second target capture DNA sequence by forming a second double strand target nucleic acid segment at a capture binding site of the second target nucleic acid fragment; (b) washing the test column to remove unbound nucleic acid fragments; (c) adding a first single strand DNA probe, which has thereon a first chemical label, to attach specifically to a probe binding site of the first target nucleic acid fragment; (d) washing the test column to remove unbound first probe; (e) adding a first triggering solution to trigger the first chemical label; (f) detecting signals generated by the first chemical label on the test snare for determining the presence of the first target nucleic acid fragment; (g) washing the test column to remove the first triggering solution; (h) adding a second single strand DNA probe, which has thereon a second chemical label, to attach specifically to a probe binding segment of the second target nucleic acid fragment; (i) washing the test column to remove unbound second probe; (j) adding a second triggering solution to trigger the second chemical label; and (k) detecting signals generated by the second chemical label on the test snare for determining the presence of the second target nucleic acid fragment.

In yet a further embodiment, the method further comprises adding least two positive control DNA sequences into the test column in step (a), wherein the test column further comprise a positive control snare which is separate spatially from the test snare by an intervening air space, and the positive control snare has thereon a positive control capture DNA sequences; and wherein the first positive control and the second positive control bind to the positive control capture DNA sequence at a capture binding site of the first and the second positive control DNA sequences; wherein in step (c) the first single strand DNA probe further attaches to a probe binding site of the first positive control DNA sequence, and in step (h) the second single strand DNA probe further attaches to a probe binding site of the second positive control DNA sequence; and wherein step (f) further comprises detecting signals generated by the first chemical label on the positive control snare for determining the presence of the first positive control DNA sequence; and step (k) further comprises detecting signals generated by the second chemical label on the positive control snare for determining the presence of the second positive control DNA sequence.

Furthermore, the positive control snare can have thereon two or more positive control capture DNA sequences, each being specific to a corresponding positive control DNA sequence. Each positive control DNA sequence binds to a corresponding positive control capture DNA sequence by forming a double strand DNA segment at a capture binding site of the positive control DNA sequence.

In an additional embodiment, the present invention provides a test column used for detection of one or more test materials. The test column has at least two snares, at least one of the snares is a test snare having thereon a capture material for detecting the presence of the test material, wherein the snares are separate spatially one from another by an intervening air space so that the snares are not in contact with one another. Furthermore, the test snare can have thereon multiple capture materials for detection of multiple test materials in the test sample, each of capture materials being specific to one of the test materials.

DETAILED DESCRIPTION OF PREFERRED EMBODIMENTS

In one embodiment, the present invention provides a method for detecting multiple test materials in a test sample using a test column. The method comprises the steps of (a) adding a test sample into a test column, the test column having at least a test snare having thereon at least two target capture materials, first target capture material being specific to a first test material in the test sample and second target capture material being specific to a second test material in the test sample; wherein the first target capture material binds with the first test material to form a bound first test material and the second target capture material binds with the second test material to form a bound second test material; (b) washing the test column to remove unbound test materials; (c) adding a first probe to attach specifically to the bound first test material, the first probe having thereon a first chemical label; (d) washing the test column to remove unbound first probe; (e) detecting signals generated by the first chemical label on the test snare for determining the presence of the first test material; (f) adding a second probe to attach specifically to the bound second test material, the second probe having thereon a second chemical label; (g) washing the test column to remove unbound second probe; and (h) detecting signals generated by the second chemical label on the test snare for determining the presence of the second test material.

The term of test material used herein means a material in a test sample for which detection is being sought. It is also referred to as target material, target nucleic acid fragment, and target DNA, RNA or PNA, depending on the specific application. The test materials particularly suitable for the method of the present invention include nucleic acids (DNA and RNA), and peptide-nucleic acid complex (PNA). Preferably, the test material is a pathogen indicator, such as DNA and RNA. The term of target capture material means a capture material that specifically binds with a test material for which detection is being sought. The target capture material is also referred to as target capture DNA when the method is used for detecting nucleic acid fragments in a test sample.

Figure 1:
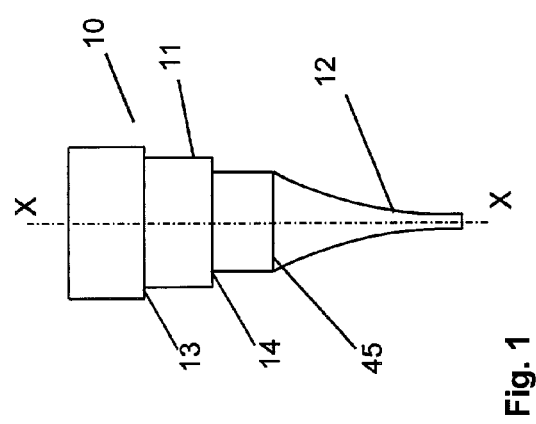
FIG. 1 shows one type of test column in one embodiment of the present invention.

FIG. 1 shows one type of the test column. Test column 10 comprises a column casing 11 and a discharge tube 12. Column casing 11 houses three snares 13, 14 and 15, which are spaced apart from one another by intervening air spaces. The snares are spaced apart along longitudinal axis X—X of column 10. Although three snares are shown in FIG. 1, there should be at least two snares in a test column. At least one of the snares is a test snare which is used for detecting the presence or otherwise of a test material in a test sample.

Snares 13, 14, and 15 may be made from any suitable material for attaching a capture material as will be explained in more detail hereinafter. Typically the snares are made from a material with high surface area, e.g. sintered glass, sintered plastic, glass fiber, beads, chips, granules, and membranes. When a membrane is used, a solid support may be required. One example of a snare is a layer of fine latex particles thereon having capture DNA sequences attached covalently, wherein the latex particles are spread out on a porous sintered glass plate. The snares may sometimes be referred herein as glass frits or a fiber chips. The column casing adjacent to the snares is light transparent, for detection of light signals from the chemical labels.

Test column 10 may take any convenient shape, cylindrical, square, rectangular, or cylindrical with one flat side. In FIG. 1, test column 10 is a step-shaped tube. Such a shape makes it necessary to make snares 13, 14 and 15 to be of different diameters. As will be described in more detail hereinafter, each of the snares may have different capture materials attached thereto to serve different detection purposes.

Figure 2:
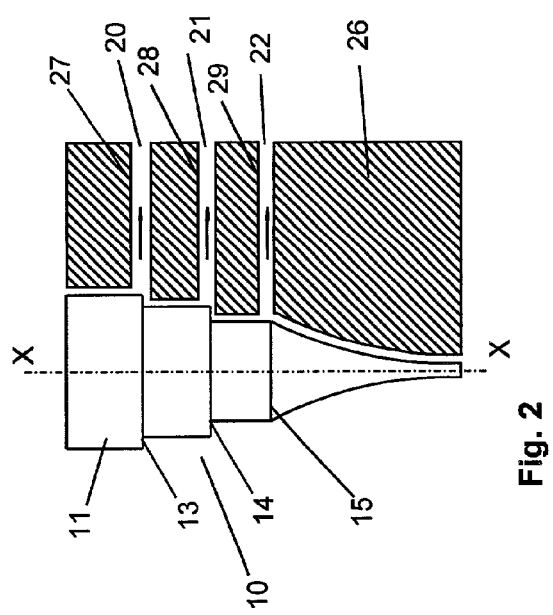
FIG. 2 shows a detector for detecting signals from a test column.

FIG. 2 shows test column 10 adjacent to a detector means. In the embodiment shown, detector block 26 is shaped to accommodate the shape of column casing 11. Detector block 26 has channels 27, 28, 29 for allowing any signals emanating from snares 13, 14, 15 to pass to detectors 20, 21 22, respectively. An advantage of the stepped column casing as shown in FIG. 2 is that signals from each of the snares are prevented from entering into an adjacent detector channel. The light detectors with appropriate wavelength can be used for detection of the signals from the chemical labels.

Figure 3:
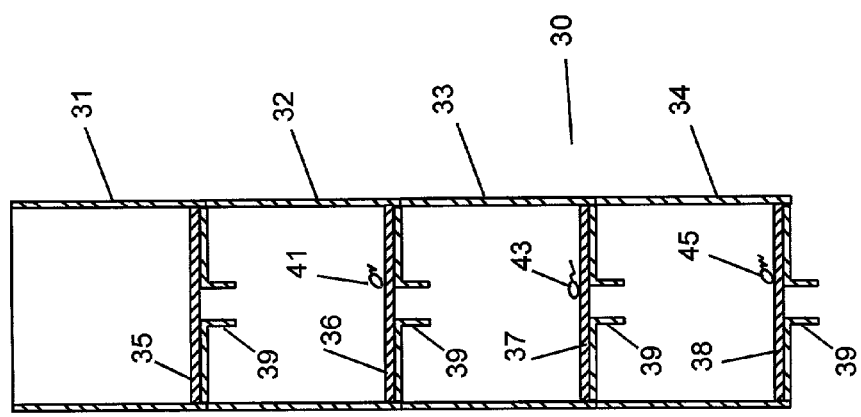
FIG. 3 shows another type of test column made with four chambers in one embodiment of the present invention.

Another type test column is shown in FIG. 3. Test column 30 is constructed from four chambers 31, 32, 33 and 34. Each chamber has a snare, i.e., 35, 36, 37, and 38, respectively. Optionally, each chamber may have a drain 39. When the snare is made of glass frit or other substance with appropriate pore size, there is no need of a drain. However, if a membrane is used as a snare, a solid support is needed and a drain can be preferred. There are connection means to connect the chambers together in a proper order. Suitable examples for ensuring connection among different chambers with correct order include having embedded slots at a specific position for different chambers, or having different numbers of slots for different chambers, or using number or color coded means.

In the embodiment shown in FIG. 3, snare 35 is a blank snare, having thereon no capture material. The blank snare is used for detecting background signals from the test sample and the process. Each of other snares, 36, 37, and 38, has thereon at least one capture material, 41, 43 and 45, respectively. In a preferred embodiment, there are multiple capture materials on each of these snares. The significance of the four chambers with their associated capture materials will be described hereinafter, particularly in relation to detection of a pathogen indicator DNA or RNA.

The chemical labels can be either fluorescence or chemiluminescence dyes. If fluorescence dyes are used, the first chemical label and the second chemical label are different, and the detections in step (e) and (h) are made at different wavelengths. If a chemiluminescence dye is used, the method further comprises additional steps of adding a first triggering solution to trigger the first chemical label prior to detecting signals in step (e); washing the test column to remove the first triggering solution prior to adding the second probe in step (f); and adding a second triggering solution to trigger the second chemical label prior to detecting signals in step (h). Furthermore, the first and second chemiluminescence labels can be the same, and then only one triggering solution is used. Herein the term of triggering solution denotes a solution, or a set of solutions, which triggers a chemiluminescence dye to release chemiluminescence signals. It is known that for some chemiluminescence dyes, the triggering solution is a single solution, but for some other chemiluminescence dyes the triggering solution involves two solutions which are sequentially added to the chemiluminescence dyes. Therefore, it should be understood that for the purpose of the present invention, the term "a triggering solution" can include a set of triggering solutions required for triggering a specific chemiluminescence dye. In a preferred embodiment, acridinium dyes are used as the chemical label. More preferably, acridinium $C_2$ NHS ester ($C_{29}H_{23}F_3N_2O_9S$, molecular weight 632.55, available from Assay Designs, Inc., Ann Arbor, Mich.) is used. The triggering solution for acridinium dye is aqueous alkaline hydrogen peroxide solutions. Commercially, the alkaline hydrogen peroxide solution is a set of two solutions. It is also possible to combine the two solution into a single solution. When the chemical label is the same, the detection in steps (e) and (h) is performed at the same wavelength. At step (e), only the first test material is being detected because the second probe carrying the chemical label has not been added into the test column. Therefore, the second test material is silent.

The method of the present invention is illustrated above with detections of two test materials in a test sample. However, the method can be used for detections of more than two test materials. When the detection is also sought for a third test material in the test sample, the test snare has thereon a third target capture material which is specific to the third test material in the test sample. Upon addition of the test sample into the test column in step (a), the third target capture material binds with the third test material to form a bound third test material. In this case, the method further comprises steps of: (i) adding a third probe to attach specifically to the bound third test material, the third probe having thereon a third chemical label; (j) washing the test column to remove unbound third probe; and (k) detecting signals generated by the third chemical label on the test snare for determining the presence of the third test material. If a chemiluminescence dye is used, the method further comprises a step of adding a third triggering solution to trigger the third chemical label before detecting signals in step (k). Furthermore, the first, second and third chemical labels can be the same, and the first, second and third triggering solutions can be the same.

In a further embodiment, for the purpose of ensuring quality and accuracy of the analysis, the method of the present invention utilizes in-line controls for each sample analyzed. The controls are added into the test column either prior to or after addition of the test sample, or added together with the test sample into the test column. The controls are processed and analyzed together with the test sample under analysis, therefore, controls can reflect the performance, and indicate any potential error of the analysis for each individual sample.

In FIGS. 1 and 3, one of the snares is a positive control snare. The positive control snare has thereon two or more positive control capture materials. The first positive control capture material is specific to the first positive control, and second positive control capture material is specific to second positive control, and so on. If two positive controls are used, upon addition of the positive controls into the test column, the first positive control capture material binds with the first positive control to form a bound first positive control, and the second positive control capture material binds with the second positive control to form a bound second positive control. In step (c) described above the first probe also attaches to the bound first positive control, and the second probe also attaches to the bound second positive control. Therefore, in step (e) the detection further includes detecting signals generated by the first chemical label on the positive control snare for determining the presence of the first positive control. Similarly, in step (h) the detection further includes detecting signals generated by the second chemical label on the positive control snare for determining the presence of the second positive control.

Furthermore, the method can further include utilizing a negative control, wherein the method further comprises adding a negative control into the test column in step (a). In this case, the test column further comprises a negative control snare which is also separate spatially from other snares by an intervening air space. The negative control snare has thereon a negative control capture material which is specific to the negative control. The negative control, upon addition, binds with the negative control capture material to form a bound negative control. Moreover, both step (e) and step (h) further comprise detecting signals generated on the negative control snare.

Additionally, the test column can have a blank snare which has no capture material thereon. The blank snare is also separate spatially from other snares by an intervening air space. The method can further comprise a detection of background signals of the test sample and the process on the blank snare of the test column.

Figure 4:
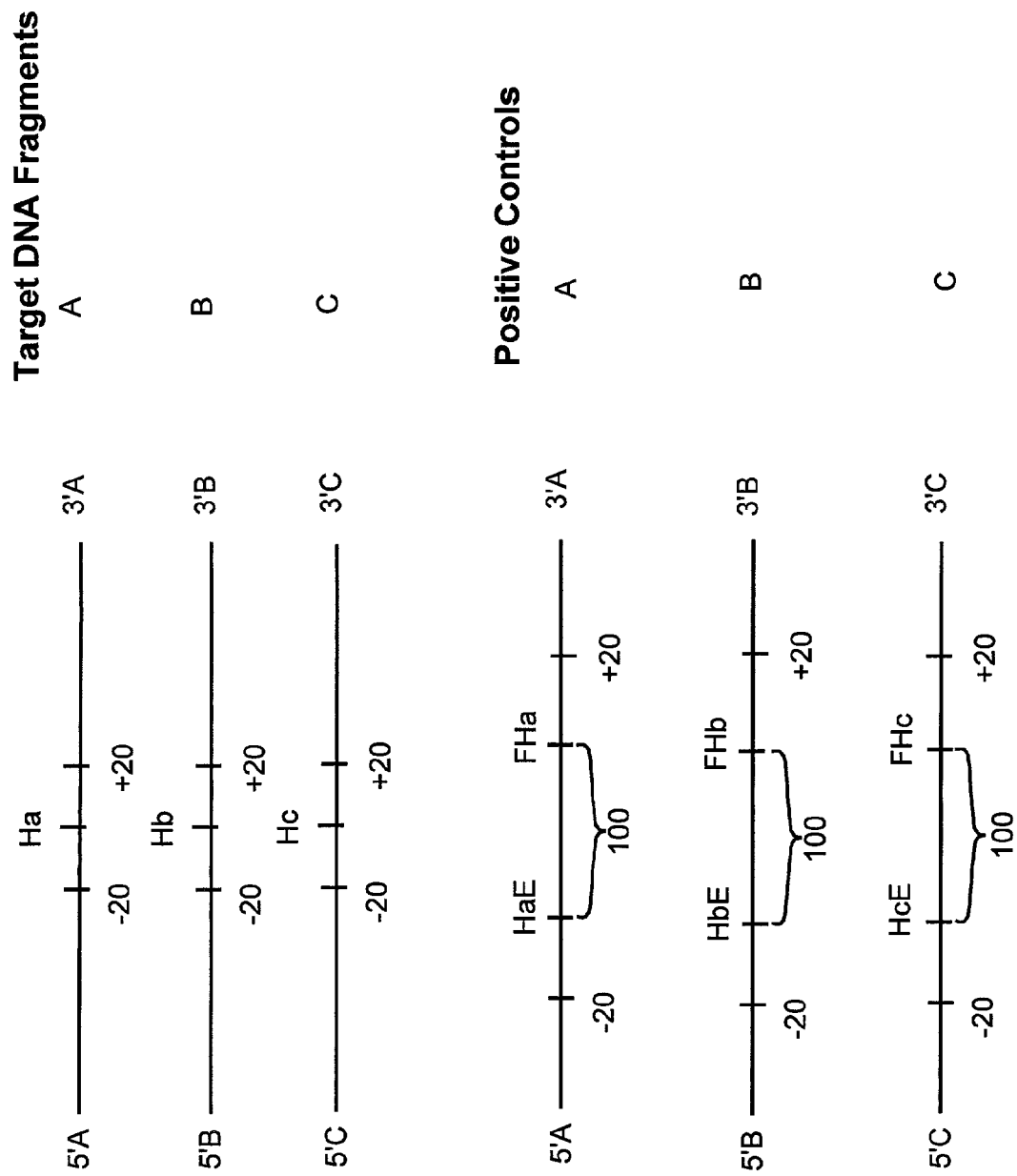
FIG. 4 illustrates schematically the design of positive control DNA sequences for analysis of target nucleic acid fragments of which the detection is sought, according to the method of the present invention.

FIG. 4 shows an example of designing a group of three positive control materials for analysis of target nucleic acid fragments in a test sample, such as pathogenic DNAs or RNAs in a patient's serum sample. Here the positive control materials are designed positive control DNA sequences.

As shown in FIG. 4, three target DNA fragments (genes) are identified as A, B, and C. These three genes represent identities of a specific pathogen, for example, *E. Coli*. The detection for these three target DNA fragments in a patient sample can assist in identifying the source of infection of the patient, which could be critical to the decision of treatment. In designing the positive controls, each of the three DNA fragments is cloned into a distinct vector. Then an insertion point H is selected in each of the three DNA fragments, as shown in FIG. 4 as Ha, Hb, and Hc, respectively. A small DNA fragment EF, for example 100 bases, is inserted into each insertion point H. An example of the inserted DNA fragment EF is a synthesized single strand DNA sequence having 100 bases. Preferably, the inserted small DNA fragment EF is the same for all positive control DNA sequences, which simplifies the design of the positive control capture sequences described below. However, the inserted small DNA fragment EF can be different for each positive control DNA sequence. Upon insertion, positive control DNA sequences A, B and C are formed, and each of the positive control DNA sequences has portions which are the same to a target DNA fragment, and a portion, i.e., fragment EF, which is different from the target DNA fragment.

Figure 5A:
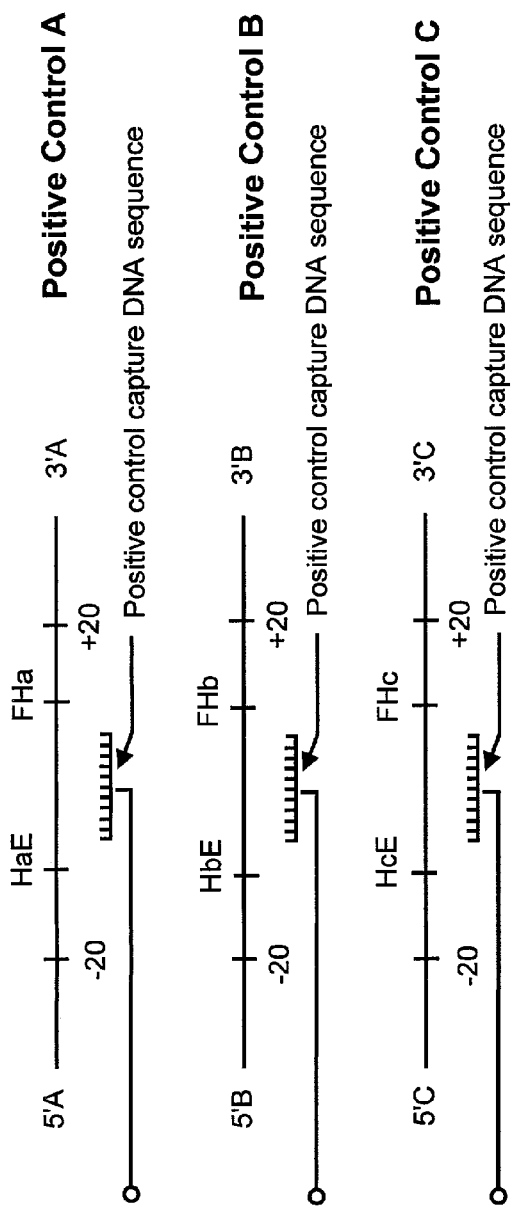
FIGS. 5A and 5B illustrate schematically the design of target capture DNA sequences, and positive control capture DNA sequences for analysis of target nucleic acid fragments of which the detection is sought, according to the method of the present invention.

On the other hand, the positive control capture materials are synthetic single strand DNA sequences which are designed to be complementary to the EF sequences of the positive control DNA sequences. When the sequence EF is the same for all positive controls, only one positive control capture sequence complementary to the EF sequence is needed, which captures all three positive control DNA sequences (A, B, and C) upon their addition into the test column. FIG. 5A illustrates interactions between each pair of positive control DNA sequences and the corresponding positive control capture sequences. In FIG. 5A, all three positive control capture DNA sequences are the same. It is understood that the action of capturing, or in another word, binding of a target or control DNA sequence to a corresponding capture DNA sequence occurs because of the complementary sequences forming a double strand DNA sequence or segment. Such a binding is very specific, and the specificity can be utilized to benefit different design purposes.

Figure 5B:
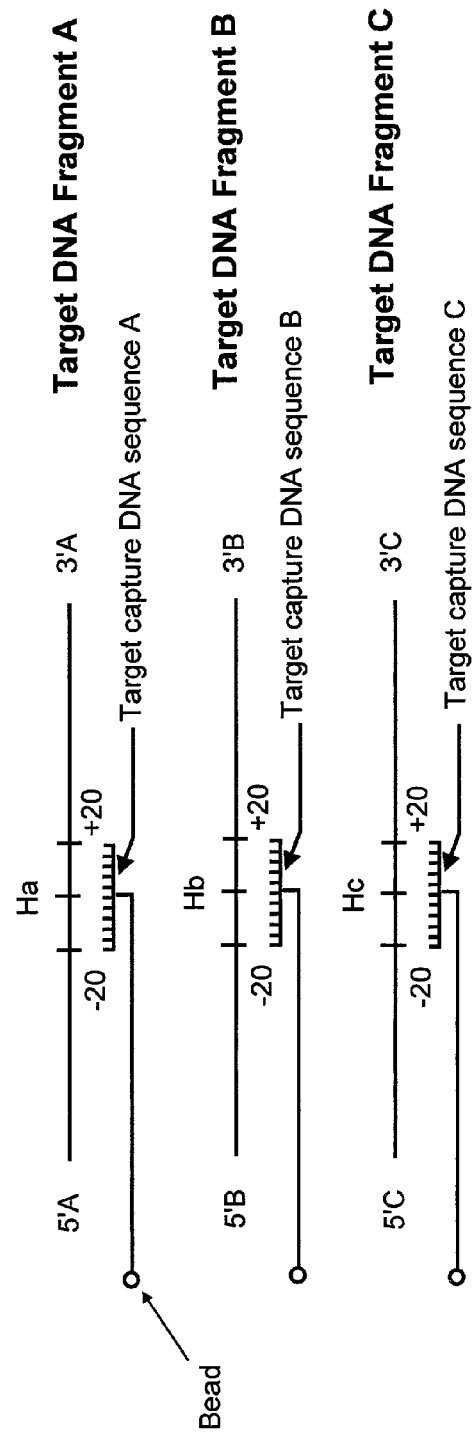

A target capture DNA sequence is a synthetic single strand DNA sequence which is designed to be complementary to a specific target DNA sequence of which the detection is sought. Each target capture DNA sequence is different from the others, for example, target capture DNA sequence A is only complementary to target DNA sequence A, and target capture DNA sequence B is only complementary to target DNA sequence B. A target capture DNA sequence is typically about forty (40) bases, selected 20 bases up stream and 20 bases down stream from the insertion point H, as shown in FIG. 5B. Although a positive control DNA sequence has portions of the sequence being the same to a target DNA sequence because the positive control is created by inserting EF sequence at the point H of the target sequence, the positive control DNA sequence lacks the continuing sequence of the original target DNA sequence that is 20 bases up stream and 20 bases down stream from the insertion point H. Therefore, a target capture DNA sequence can only capture a corresponding target DNA sequence, but not a positive control DNA sequence; and a positive control capture sequence can only capture a corresponding positive control DNA sequence, but not a target DNA sequence. Such a difference in complementary binding is illustrated in FIGS. 5A and 5B.

For analysis of nucleic acid fragments in a test sample, the negative control is a synthetic single strand DNA sequence that is different from the target DNA sequences, and different from the positive control DNA sequences. The negative control capture material is a synthetic single strand DNA sequence which is designed to be complementary to the negative control DNA sequence. When the negative control DNA sequence is added into the test column, it can only be captured by the negative control capture DNA sequence on the negative control snare. The negative control DNA sequence does not interact with either the target capture DNA sequences on the test snare, or the positive control DNA sequences on the positive control snare.

Figure 6:
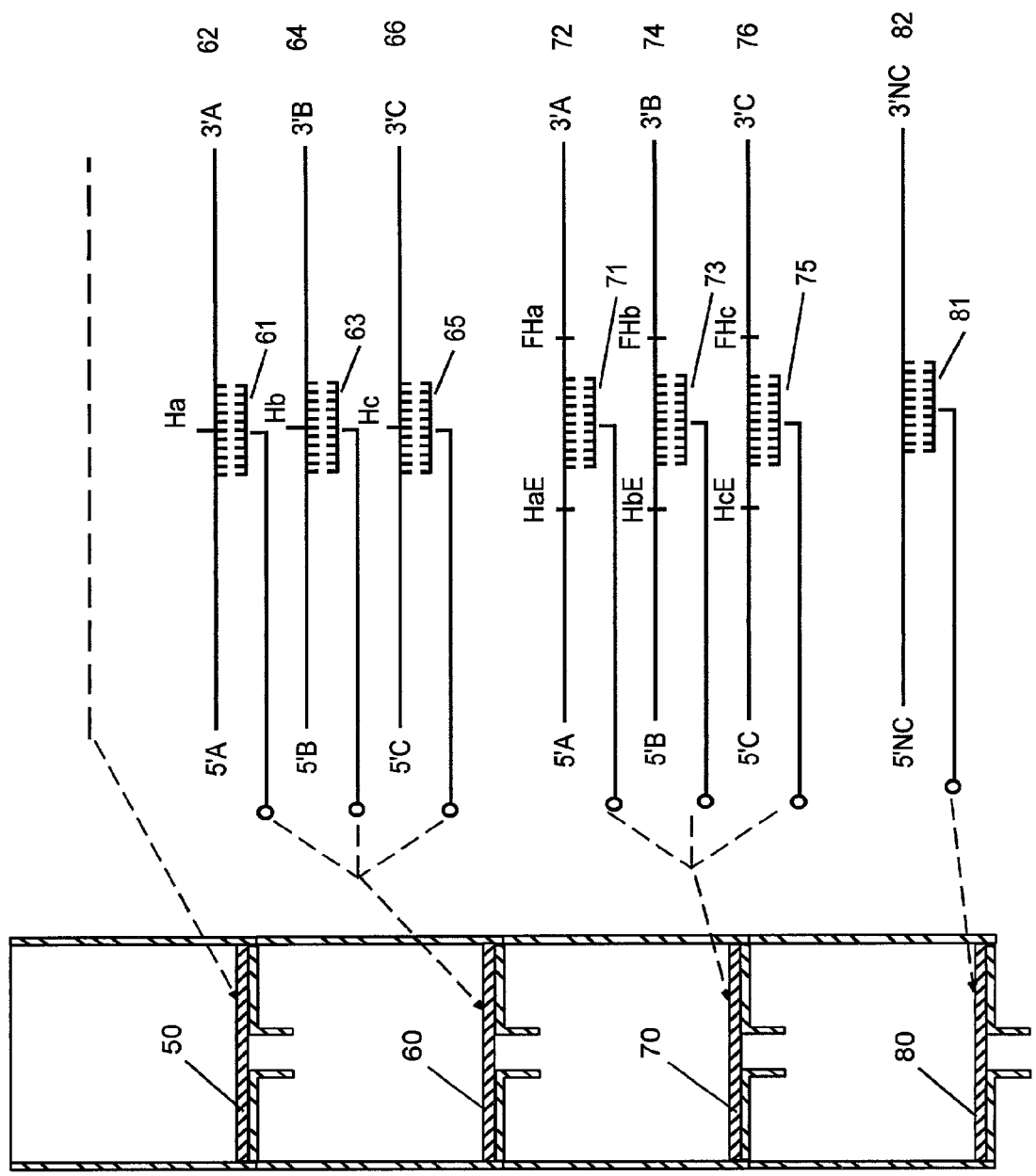
FIG. 6 illustrates schematically the binding of three target DNA fragments and controls to the capture DNA sequences after addition of a test sample and controls into a test column, according to the method of the present invention.

FIG. 6 to 12 illustrate a process of analyzing three target DNA fragments in a test sample using the method of the present invention. As shown in FIG. 6, the test column has four snares, blank snare 50, test snare 60, positive control snare 70 and negative control snare 80. On test snare 60 there are three target capture DNA sequences, 61, 63, and 65. On the positive control snare 70 there are three positive control capture DNA sequences 71, 73, and 75. On negative control snare 80 there is a negative control capture DNA sequence 81. No capture DNA sequence is on snare 50.

FIG. 6 shows the bindings on each snare after a test sample, a positive control and a negative control are added into the test column. The test sample contains three single strand target DNA fragments, 62, 64, and 66. The positive control contains three positive control single strand DNA sequences, 72, 74 and 76. The negative control contains a negative control single strand DNA sequence, 81. The natural target DNAs in a sample are in a double strand form, which are denatured by a common method and reagents known in the art, to form a single strand target DNA fragment. This is performed in the sample preparation stage prior to adding the test sample into the test column.

The test sample and controls are in a liquid form, and flow down the column and pass through all snares. Upon contacting with the snares, target capture DNA sequence 61 captures target DNA fragment 62, target capture DNA sequence 63 captures target DNA fragment 64, and target capture DNA sequence 65 captures target DNA fragment 66, respectively. Each target DNA sequence forms a double strand DNA segment at the capture binding site of the target DNA sequence with the corresponding target capture DNA sequence. Herein the term of capture binding site means a segment of nucleic acid sequence in the target or control sequences, that is complimentary to a corresponding capture DNA sequence. As shown in FIG. 6, the capture binding sites of the target DNA fragments are at the H point, shown as Ha, Hb, and Hc for the three target DNA fragments, respectively.

Similarly, positive control capture DNA sequence 71 captures positive control DNA sequence 72, positive control capture DNA sequence 73 captures positive control DNA sequence 74, and positive control capture DNA sequence 75 captures positive control sequence 76, respectively. Each positive control DNA sequence forms a double strand DNA segment at the capture binding site of the positive control DNA sequence with the corresponding positive control capture DNA sequence. Further, the negative control capture DNA sequence 81 captures negative control DNA sequence 82, and forms a double strand DNA segment at the capture binding site of the negative control DNA sequence. Since no capture material is present on the blank snare, no specific binding of the target DNA fragments or controls occurs on the blank snare. The broken lines marked for snare 50 in FIG. 6 to FIG. 12 denote no specific capture interaction occurs on this snare.

After addition of the test sample and controls, the test column is washed with a wash solution to wash out unbound target DNA fragments and unbound control DNA sequences. A wash solution composition known in the art for nucleic acid analysis can be used in the process described above, so long as the components of the wash solution are compatible with the chemical labels used for the detections.

Figure 7:
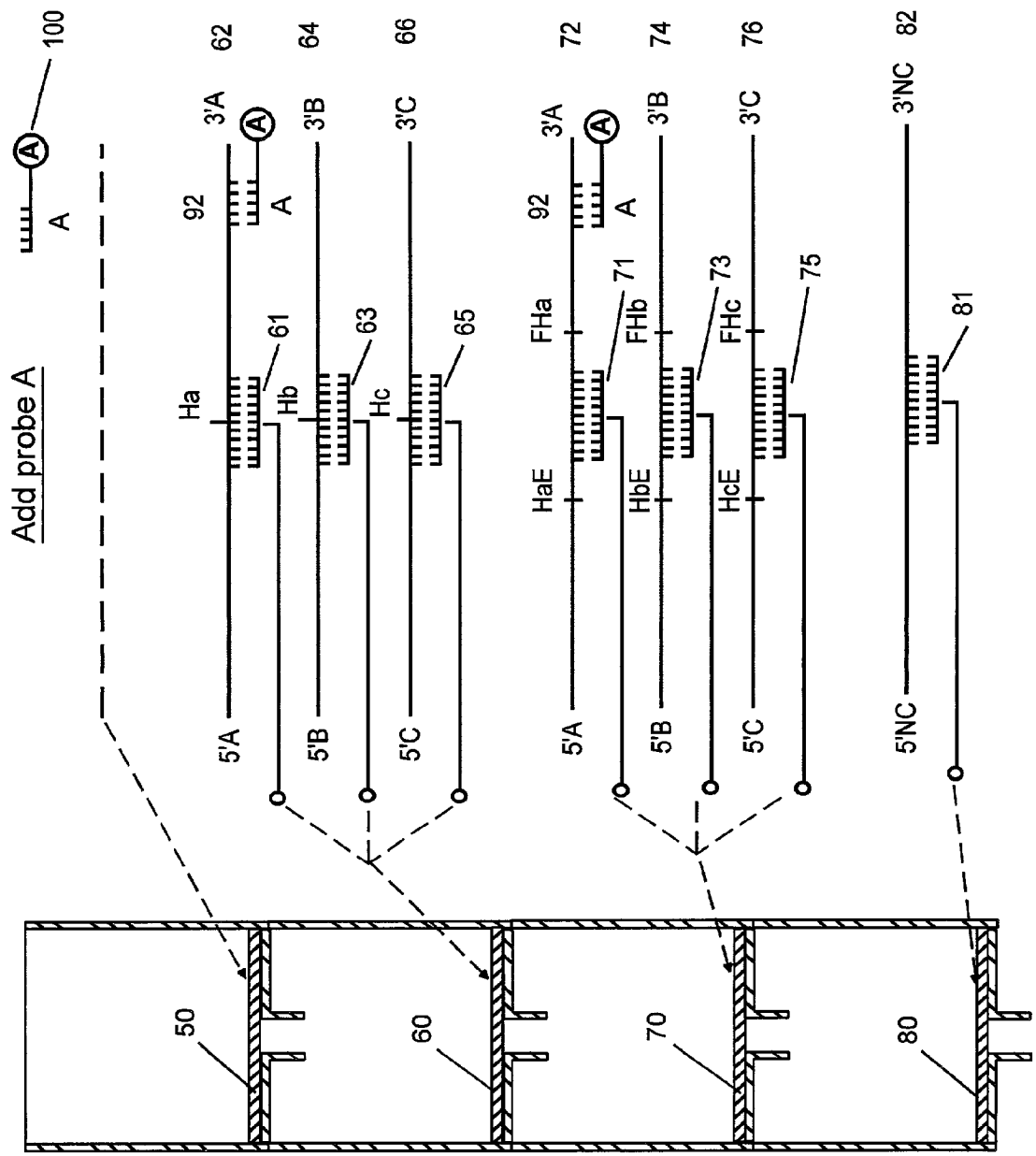
FIG. 7 illustrates schematically the selective binding of DNA probe A with a first target DNA fragment and a first positive control DNA sequence, according to the method of the present invention.

Subsequent to the washing, probe A, is added into the test column. Probe A is a single strand DNA sequence complementary to a segment of target fragment 62 and of positive control sequence 72. The probe A has thereon a chemical label 100. In this example, chemical label 100 is a chemiluminescence dye. As shown in FIG. 7, probe A binds to a probe binding site 92 of target DNA fragment 62 and positive control DNA sequence 72. Herein the term of probe binding site means a segment of the nucleic acid sequence in the target or control DNA sequences, that is complimentary to the probe sequence. The binding site is the same for target DNA fragment 62 and positive control DNA sequence 72. In FIG. 7, for the convenience of illustration, the probe binding site 92 is positioned at one end of the target and positive control DNA sequences. However, it is understood that the probe binding site can be at other locations of the target and positive control DNA sequences. Since only target DNA sequence 62 and positive control DNA sequence 72 have probe binding site 92 for probe A, probe A does not bind to other target DNA fragments, or other positive control DNA sequences. As described previously, the negative control DNA sequence is different from the target DNA fragments, and also different from the positive control DNA sequences. It does not have probe binding site 92 for probe A. Therefore, probe A does not bind to negative control DNA sequence 82 either.

Figure 8:
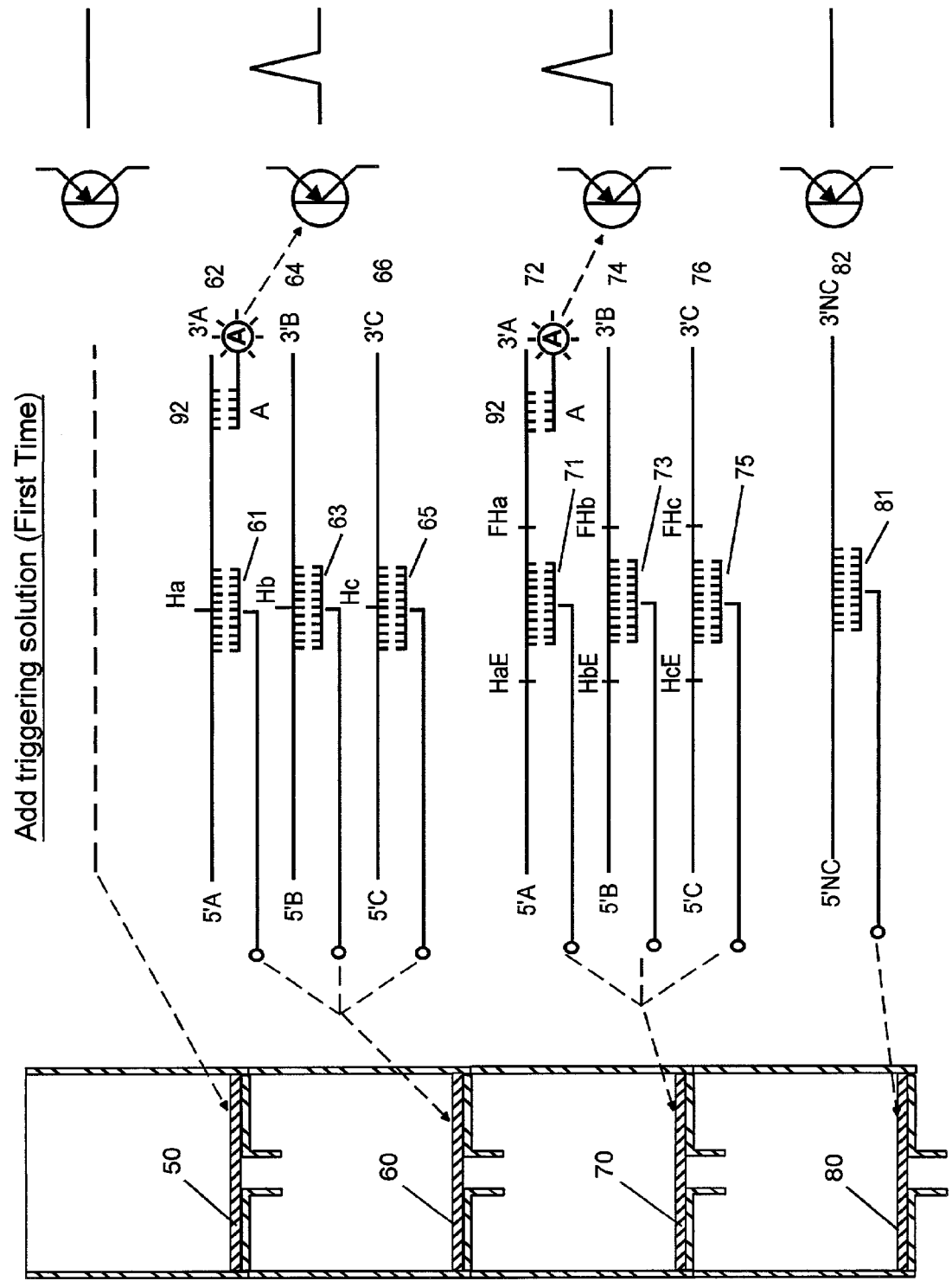
FIG. 8 illustrates schematically triggering of the chemiluminescent label on probe A and detection of the signals on four snares of the test column for detection of the first target DNA fragment in the test sample, according to the method of the present invention.

The test column is then washed with the wash solution to wash out unbound probe A. Thereafter, a triggering solution of chemical label 100 is added into the test column. The triggering solution triggers the chemiluminescence dye instantly, and the dye releases chemiluminescent signals on test snare 60 and on positive control snare 70. The chemiluminescent signals are detected by an optical detector. The detections are performed on all four snares simultaneously at the same emitting wavelength of the chemiluminescence dye, as illustrated in FIG. 8. The presence, or absence of signals on test snare 60 indicates the presence of target DNA fragment 62. Further, the intensity of the signals on test snare 60 reflects the amount of target DNA fragment 62 in the test sample, which is used for quantitation of the target fragment. The presence of signals on positive snare 70 indicates proper process conditions of the method. Moreover, the intensity of the signals on positive snare 70, corresponding to the known amount of positive control 72 added, further reflects proper conditions of the process. If signals are detected on blank snare 50, which reflects background noises of the process, it can be used in data analysis to adjust detection results obtained on the test snare and the control snares. On the other hand, since probe A does not bind to negative control 82, no signal should be detected on negative control snare 80, if the sample analysis process performs properly.

Figure 9:
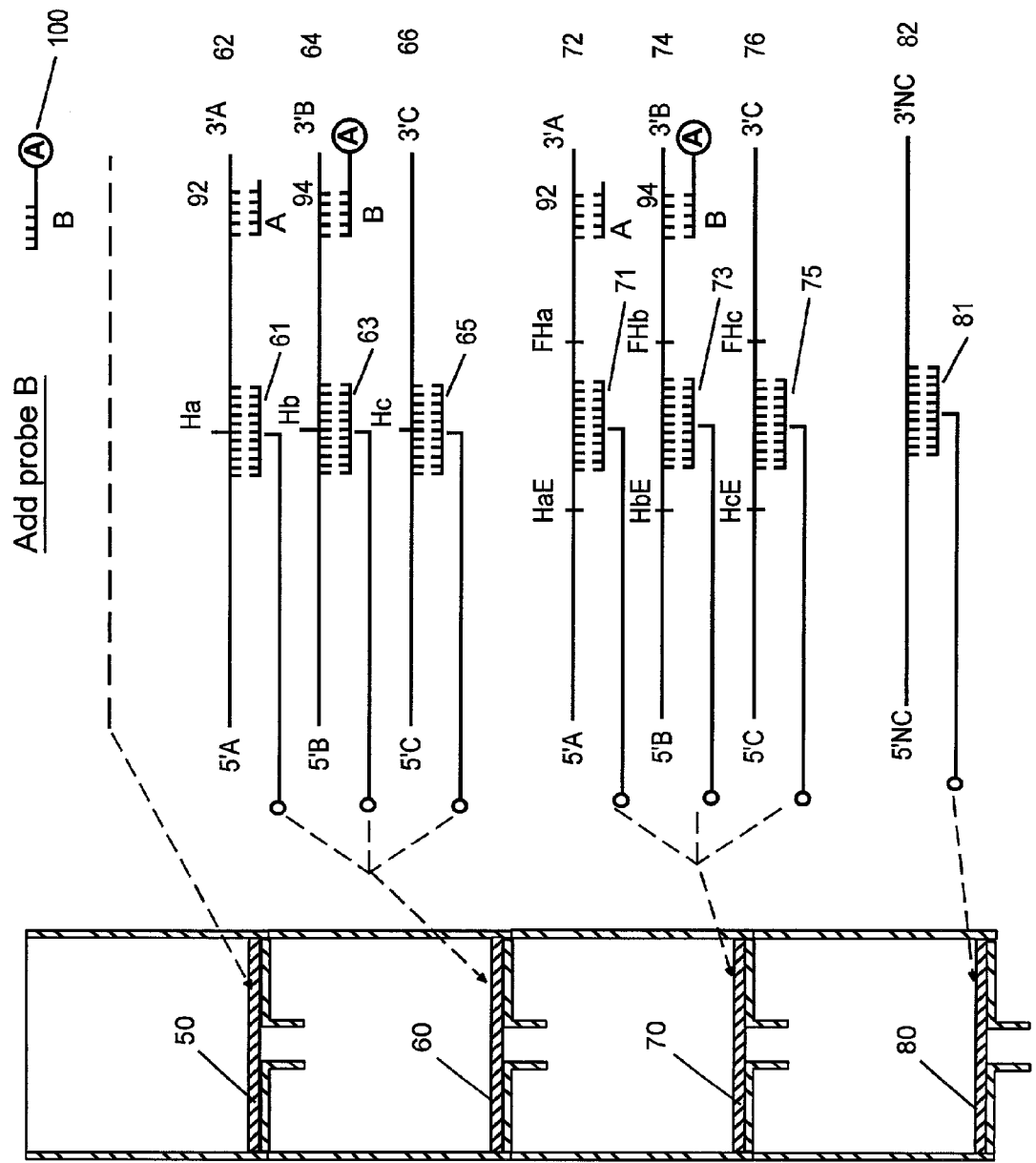
FIG. 9 illustrates schematically the selective binding of DNA probe B with a second target DNA fragment and a second positive control DNA sequence, according to the method of the present invention.
Figure 10:
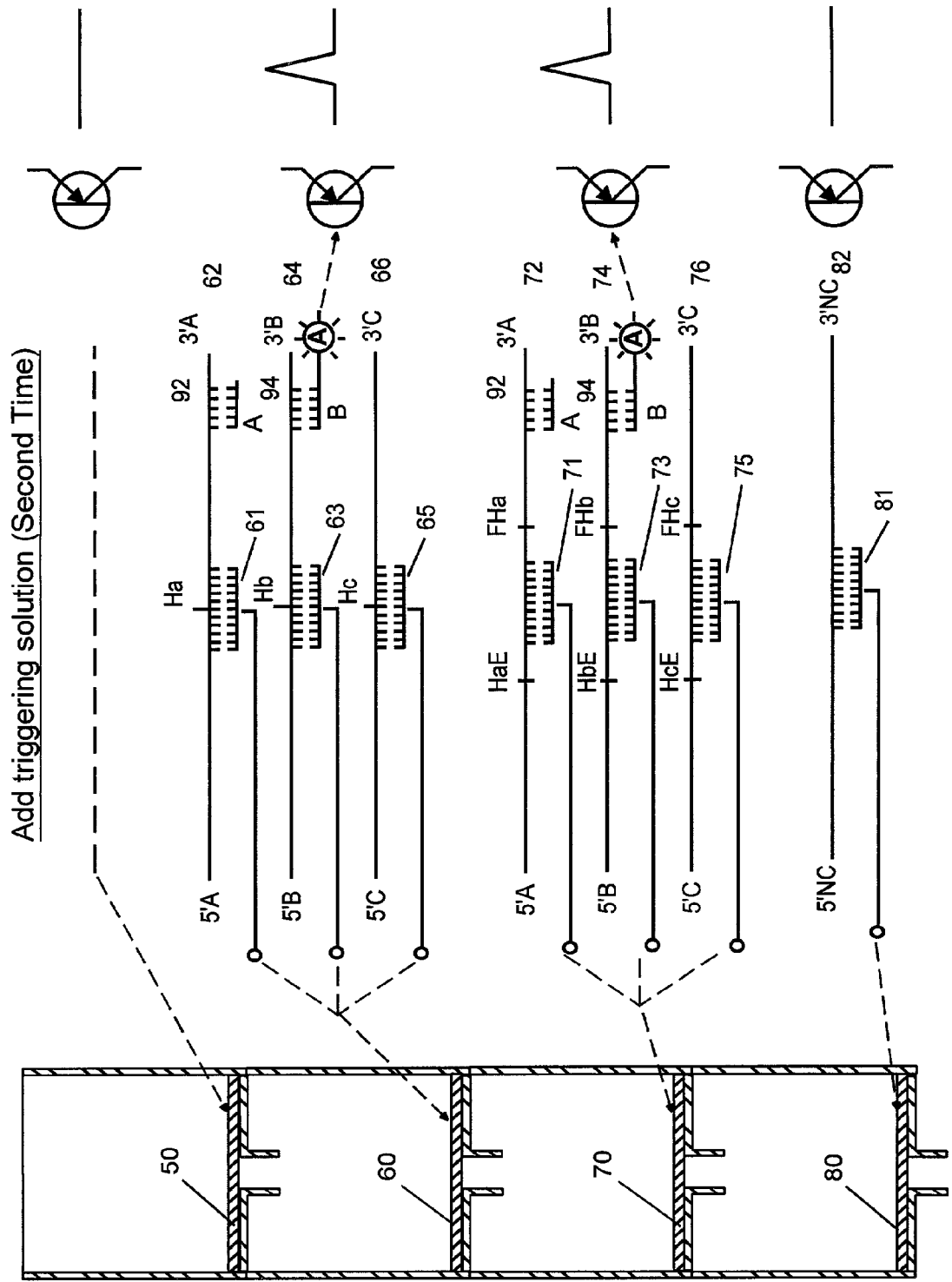
FIG. 10 illustrates schematically triggering of the chemiluminescent label on probe B and detection of the signals on four snares of the test column for detection of the second target DNA fragment in the test sample, according to the method of the present invention.

After detection of target DNA fragment 62, the test column is washed to wash out the triggering solution. Then, probe B is added into the test column. In this example, probe B carries the same chemical label 100. Similar to the process described above, probe B binds specifically to a probe binding site 94 of target DNA fragment 64 and positive control DNA sequence 74, as shown in FIG. 9. Following a wash, to wash out unbound probe B, the same triggering solution is added again into the test column. The second detection is performed on all four snares in the same manner described above, as illustrated in FIG. 10. At this time, probe A on test snare 60 and positive control snare 70 is silent after the chemiluminescence dye has released its energy during the first triggering. Furthermore, since probe B binds specifically to probe binding site 94 which only presents in target DNA fragment 64 and positive control DNA sequence 74, it does not binds to target DNA fragments 62 and 66, or positive control DNA sequences 72 and 76. Therefore, the second detection is specific for the presence of target DNA fragment 64 in the test sample, although the detection is performed in the same wavelength of the first detection. For detection of target DNA fragment 64, blank snare 50 and negative control DNA sequence 82 have the same function as in the first detection.

It is important to note that the use of positive control DNA sequence 74 specifically reflects the performance of the analysis process for detection of target DNA fragment 64, which would not be reflected by using positive control DNA sequence 72, because the later does not share probe binding site 94 of target DNA fragment 64. Therefore, the method of the present invention monitors the process for detection of each individual target DNA fragment, by a true in-line control for each step of the sample analysis.

Figure 11:
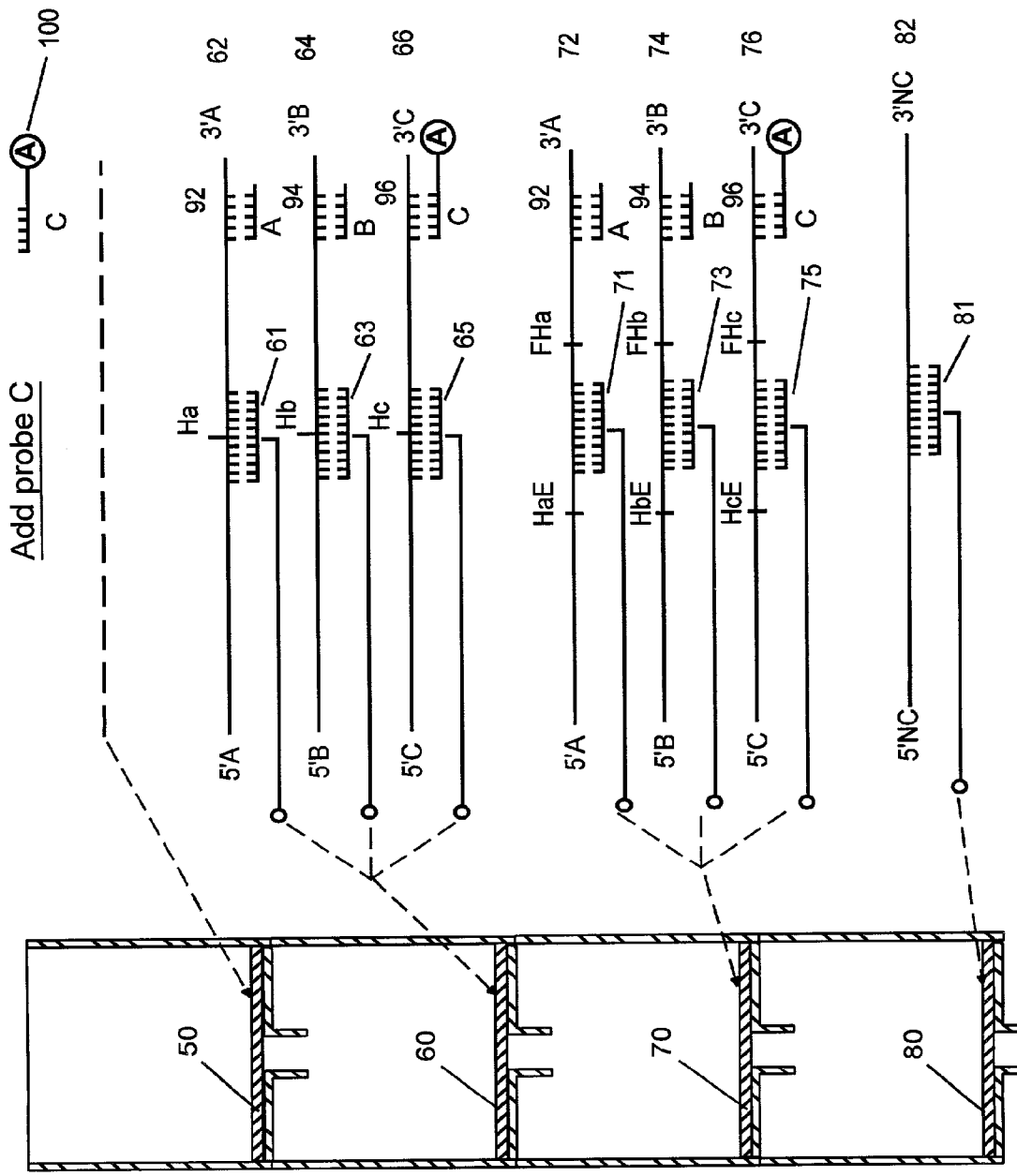
FIG. 11 illustrates schematically the selective binding of DNA probe C with a third target DNA fragment and a third positive control DNA sequence, according to the method of the present invention.
Figure 12:
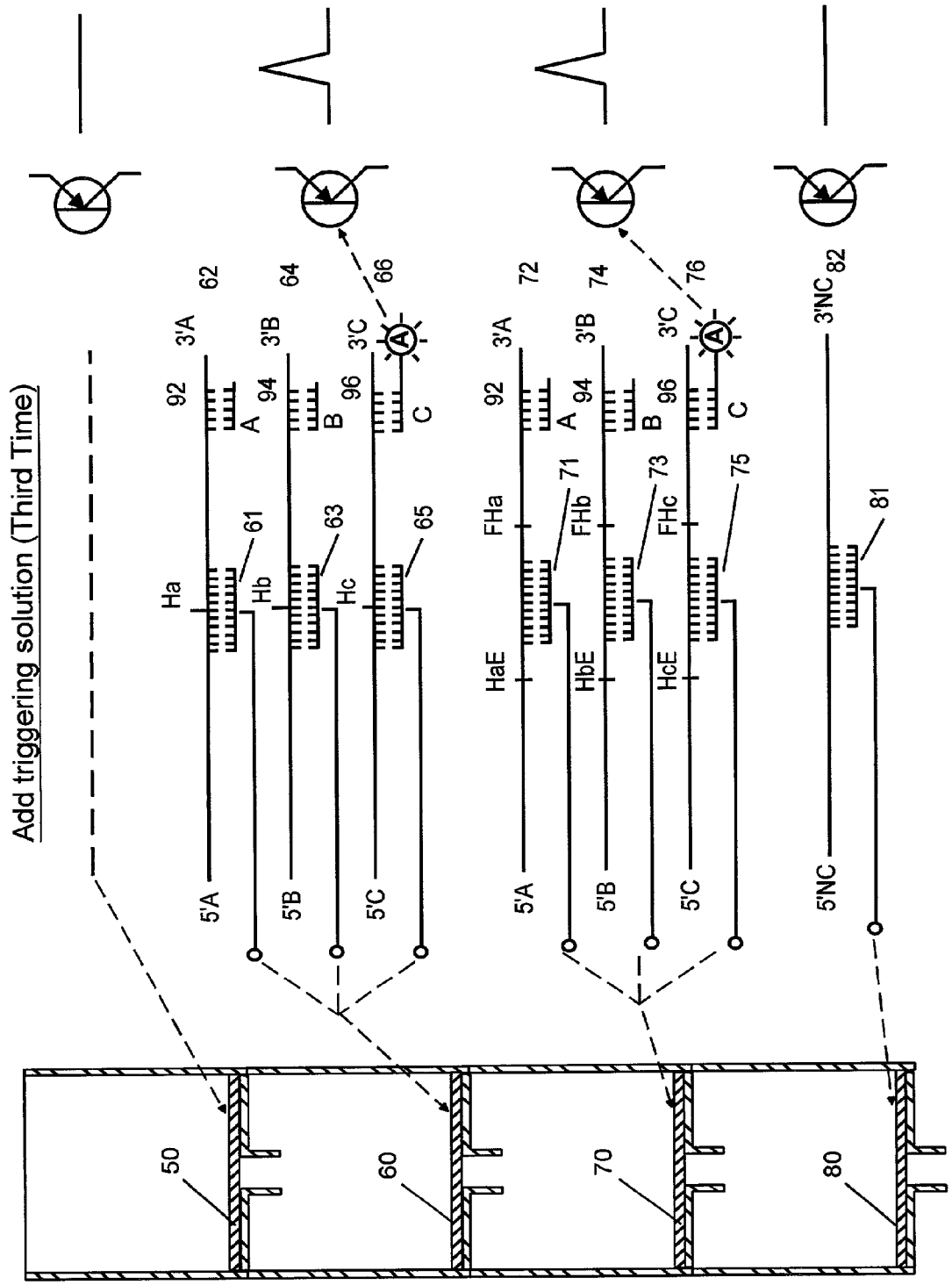
FIG. 12 illustrates schematically triggering of the chemiluminescent label on probe C and detection of the signals on four snares of the test column for detection of the third target DNA fragment in the test sample, according to the method of the present invention.

After detection of target DNA fragment 64, the test column is washed with the wash solution to wash out the triggering solution. Then, probe C is added into the test column, which carries the same chemical label 100. Probe C binds specifically to a probe binding site 96 of target DNA fragment 66 and positive control DNA sequence 76, as shown in FIG. 11. Following a wash, to wash out unbound probe C, the same triggering solution is added the third time into the test column. The third detection is performed on all four snares in the same manner described previously, as illustrated in FIG. 12. Now both probes A and B on test snare 60 and positive control snare 70 are silent. Similar to the other two probes' reactions, probe C binds specifically to probe binding site 96 which only presents in target DNA fragment 66 and positive control DNA sequence 76. Therefore, the third detection is specific for the presence of target fragment 66 in the test sample. The blank snare 50 and negative control DNA sequence 82 have the same function as in the previous detections.

In this example, probe A, B, and C carry the same chemical label. However, it should be understood that each of the probes can carry different chemical labels, and accordingly different triggering solutions can be used.

For all three detections, there should be no signals on negative control snare 80 if the sample analysis process functions properly. The negative control is a secondary control, however, it provides important information in addition to that obtained from a positive control. Under normal conditions, the negative control snare should never produce a signal. If a signal is detected from a negative control snare, it may indicate several potential problems. For example, (1) the probe is not specific enough; (2) the test column is blocked or a wash cycle is not complete; (3) wash solution is contaminated; or (4) the sample is contaminated, such as an increased fluorescein concentration due to specific type of food or drug taken by the patient.

As indicated hereinbefore, it is possible that the signals detected from the controls and any target nucleic acid fragments can be subject to some background interference caused by interaction of other materials in the test sample with the snare material. The background interference can be detected from snare 50 which is independent of the controls or the target nucleic acid fragments. Therefore, the signals obtained from detection of the controls or the target nucleic acid fragments can be adjusted accordingly to take into account the interference.

The method of analyzing target nucleic acids of a test sample has been illustrated by using DNA fragments. It is understood that the method can be utilized for analysis of RNAs in a test sample. When the target nucleic acid is RNA, denaturing process described above for double strand DNA is not needed. The single strand RNA in the test sample is used directly for the analysis. In the current PCR method, it is necessary to isolate the RNA and convert the RNA into cDNA. This leads to loss and/or degradation of the RNA. Sometimes the loss of RNA can be greater than 90%. The method of the present invention overcomes this problem and provides an enhanced efficiency wherein very little, if any, RNA is lost.

The analysis process of the present invention can be completely automated, including the addition of test sample and controls, addition of reagents and wash solution, detection of signals, data analysis and report, as well as load and unload of test columns. Suitable instruments for the instant method are disclosed in U.S. Pat. No. 6,174,733 and copending U.S. patent applications Ser. Nos. 09/093,532 and 09/671,398, all of which are incorporated by reference in their entirety.

The method of the present invention has broad applications in clinical diagnosis, research, environmental test, food industry, and other industries. Clinical applications include, but are not limited to, diagnostic analyses relating to cancer, auto-immune diseases, infectious diseases, haemostasis, and veterinary medicine. For example, the DNA method of the present invention can be used for diagnosis of N. gonorrhoea, H. ducreyi, trepona pallidum, human papillomavirus (HPV), herpes simplex virus (HSV), molluscum contagiosum (MC), trichomonas vaginalis, and the RNA method may be used for diagnosis of human immunodeficiency virus (HIV). In environmental and food industry, the method of the present invention can be used for detection of water or food contaminations, such as common contamination of *E. coli*.

The method of the present invention has several advantages over the currently known analysis methods. With the method of present invention, a single chemical label can be used for detections of multiple target materials and multiple control materials. This can significantly simplify the detector design, and reduces instrument cost. It can further reduce the possibility of cross contamination among different chemical labels, and reduce research and development, and manufacturing costs for developing and manufacturing the labeled probes. Moreover, with a single chemical label, only one triggering solution is needed. Therefore, the reagents and inventory costs for the users are reduced. Furthermore, the instant method saves analysis time and labor involved, because the detections for multiple target materials are performed in one automated process. Therefore, it is convenient and also less costly.

Moreover, the instant method requires less sample volume in comparison to the existing analysis methods, because detection of multiple target materials is performed using one aliquot of sample. As described previously, for detecion of *E. coli* contaminations, at least three genes are required to be analyzed in a sample. Currently, each of the multiple genes is analyzed separately, and hence, each test requires one aliquot of sample. It is well understood that a smaller sample volume is strongly demanded in the clinical tests. Sometimes, a smaller sample volume is necessary because of multiple diagnostic tests being requested for one blood sample. At other times, there is simply limited volume of a sample available, such as in the instance of analyzing a new born baby's blood, which necessitates a small sample volume.

On the other hand, the method of the present invention utilizes multiple in-line controls, each of which reflects reaction conditions in detection of a corresponding target material. As described previously, because the controls share each step of the reactions and detection of the target materials, and the positive controls further share the probe binding sites with the target nucleic acid sequences, the instant method provides true in-line controls. Therefore, the method provides high detection reliability and accuracy, and reduces the risk of error.

In an additional aspect, the present invention provides the test columns used for the method of the present invention. The test column has at least two snares, and at least one of the snares is a test snare having thereon a target capture material for detecting the presence of the test material. The snares are separate spatially by intervening air spaces. For detection of multiple test materials in a test sample as described above, the test snare has thereon two or more target capture materials. Furthermore, the test column further includes a positive control snare which has thereon two or more positive control capture materials, each being specific to one positive control used for a detection process being sought for. Moreover, the test column can also have a negative control snare, and a blank snare.

The test column can also be provided in a kit, which comprises (a) a test column, (b) controls, and (c) reagents for detecting the presence of the test materials. The kit can further include instructions, on or associated with the kit, for the specific test materials of which the detections are sought for.

The invention has been described with reference to the preferred embodiments. It should be understood, however, that the invention is not so limited, and the scope of the invention should be determined with reference to the following claims, rather than to the foregoing specification.

What is claimed is:

1. A method for sequentially detecting multiple target nucleic acid fragments in a test sample comprises the steps of:
    (a) adding a test sample containing single strand target nucleic acid fragments into a test column, said column having a plurality of snares which are spaced apart along a longitudinal axis of said column and separated one from another by an intervening air space; at least one of said snares being a test snare having thereon at least two different single strand target capture DNA sequences, a first target capture DNA sequence being specific to a first target nucleic acid fragment in said test sample and a second target capture DNA sequence being specific to a second target nucleic acid fragment in said test sample; and wherein said first target nucleic acid fragment binds to said first target capture DNA sequence on said snare by forming a double strand target nucleic acid segment at a capture binding site of said first target nucleic acid fragment and said second target nucleic acid fragment binds to said second target capture DNA sequence on said snare by forming a double strand target nucleic acid segment at a capture binding site of said second target nucleic acid fragment;
    (b) washing said test column to remove unbound nucleic acid fragments;
    (c) adding a first single strand DNA probe to attach specifically to a probe binding site of said first target nucleic acid fragment, said first probe having thereon a first chemical label;
    (d) washing said test column to remove unbound first probe;
    (e) adding a first triggering solution to trigger said first chemical label;
    (f) detecting signals generated by said first chemical label on said test snare for determining the presence of said first target nucleic acid fragment;
    (g) washing said test column to remove said first triggering solution;
    (h) adding a second single strand DNA probe to attach specifically to a probe binding site of said second target nucleic acid fragment, said second probe having thereon a second chemical label;
    (i) washing said test column to remove unbound second probe;
    (j) adding a second triggering solution to trigger said second chemical label; and (k) detecting signals generated by said second chemical label on said test snare for determining the presence of said second target nucleic acid fragment.

2. The method of claim 1, wherein said nucleic acid fragments comprise DNA, RNA, and PNA.

3. The method of claim 1, wherein said chemical labels chemiluminescence labels.

4. The method of claim 3, wherein said chemical labels are an acridinium dye.

5. The method of claim 1, wherein said test snare has thereon a third target capture DNA sequence being specific to a third target nucleic acid fragment in said test sample; wherein said third target nucleic acid fragment binds to said third target capture DNA sequence by forming a double strand target nucleic acid segment at a capture binding site of said third target nucleic acid fragment; and wherein said method further comprises steps of:
  (l) washing said test column to remove said second triggering solution;
  (m) adding a third single strand DNA probe to attach specifically to a probe binding site of said third target nucleic acid fragment, said third probe having thereon a third chemical label;
  (n) washing said test column to remove unbound third probe;
  (o) adding a third triggering solution to trigger said third chemical label; and
  (p) detecting signals generated by said third chemical label on said test snare for determining the presence of said third target DNA sequence.

6. The method of claim 1, wherein step (a) further comprises adding least two positive control DNA sequences into said test column, said test column further comprising a positive control snare which is separate spatially from said test snare by an intervening air space; and said positive control snare having thereon a positive control capture DNA sequence; wherein a first positive control DNA sequence and a second positive control DNA sequence bind to said positive control capture DNA sequence by forming a double strand DNA segment at a capture binding site of said first and said second positive control DNA sequences; and wherein in step (c) said first single strand DNA probe further attaches to a probe binding site of said first positive control DNA sequence, and in step (h) said second single strand DNA probe further attaches to a probe binding site of said second positive control DNA sequence; and wherein step (9 further comprises detecting signals generated by said first chemical label on said positive control snare for determining the presence of said first positive control DNA sequence: and step (k) further comprises detecting signals generated by said second chemical label on said positive control snare for determining the presence of said second positive control DNA sequence.

7. The method of claim 6, wherein said probe binding site of said first positive control DNA sequence is same to said probe binding site of said first target nucleic acid fragment, and said probe binding site of said second positive control DNA sequence is same to said probe binding site of said second target nucleic acid fragment.

8. The method of claim 6, wherein said positive control snare having thereon two positive control capture DNA sequences, a first positive control capture DNA sequence being specific to first positive control DNA sequence and a second positive control capture DNA sequence being specific to second positive control DNA sequence; wherein said first positive control DNA sequence binds to said first positive control capture DNA sequence at a capture binding site of said first positive control DNA sequence and said second positive control DNA sequence binds to said second positive control capture DNA sequence at a capture binding site of said second positive control DNA sequence.

9. The method of claim 6, wherein said test snare has thereon a third target capture DNA sequence being specific to a third target nucleic acid fragment in said test sample, and said third target nucleic acid fragment binds to said third target capture DNA sequence by forming a double strand target nucleic acid segment at a capture binding site of said third target nucleic acid fragment; and wherein step (a) further comprises adding a third positive control DNA sequence into said test column, and said third positive control DNA sequence binds to said positive control capture DNA sequence at a capture binding site of said third positive control DNA sequence;
  and wherein said method further comprises steps at
  (l) washing said test column to remove said second triggering solution;
  (m) adding a third single strand DNA probe to attach specifically to a probe binding site of said third target nucleic acid fragment and to a probe binding site of said third positive control DNA sequence, said third probe having thereon a third chemical label;
  (n) washing said test column to remove unbound third probe;
  (o) adding a third triggering solution to trigger said third chemical label; and
  (p) detecting signals generated by said third chemical label on said test snare and said positive control snare for determining the presence of said third target DNA sequence and said third positive control DNA sequence.

10. The method of claim 1, wherein step (a) further comprises adding a negative control DNA sequence into said test column, said test column further comprising a negative control snare which is separate spatially from other snares by an intervening air space, and said negative control snare having thereon a negative control capture DNA sequence which is specific to said negative control DNA sequence; wherein said negative control DNA sequence binds to said negative control capture DNA sequence by forming a double strand negative control DNA segment at a capture binding site of said negative control DNA sequence; and wherein step (f) and (k) further comprise detecting signals generated on said negative control snare.

11. A method for sequentially detecting multiple target nucleic acid fragments in a test sample comprises the steps of:
  (a) adding two positive control DNA sequences and a test sample containing single strand target nucleic acid fragments into a test column, said test column having at least two snares which are spaced apart along a longitudinal axis of said column and separated one from another by an intervening air space; at least one of said snares being a test snare, one of said snares being a positive control snare; said test snare having thereon at least two different target capture DNA sequences, a first target capture DNA sequence being specific to a first target nucleic acid fragment in said test sample and a second target capture DNA sequence being specific to a second target nucleic acid fragment in said test sample; said positive control snare having thereon a positive control capture DNA sequence; and wherein said first target nucleic acid fragment binds to said first target capture DNA sequence by forming a double strand target nucleic acid segment at a capture binding site of said first target nucleic acid fragment, and said second target nucleic acid fragment binds to said second target capture DNA sequence by forming a second double strand target nucleic acid segment at a capture binding site of said second target nucleic acid fragment; said first positive control DNA sequence and said second positive control DNA sequence bind to said positive control capture DNA sequence at a capture binding site of said first and said second positive control DNA sequences;

(b) washing said test column to remove unbound nucleic acid fragments and unbound positive control DNA sequences;

(c) adding a first single strand DNA probe to attach specifically to a probe binding site of said first target nucleic acid fragment and a probe binding site of said first positive control DNA sequence, said first probe having thereon a chemical label;

(d) washing said test column to remove unbound first probe;

(e) adding a triggering solution to trigger said chemical label;

(f) detecting signals generated by said chemical label on said test snare and said control snare for determining the presence of said first target nucleic acid fragment and said first positive control DNA sequence;

(g) washing said test column to remove said triggering solution;

(h) adding a second single strand DNA probe to attach specifically to a probe binding site of said second target nucleic acid fragment and a probe binding site of said second positive control DNA sequence, said second probe having thereon said chemical label;

(i) washing said test column to remove unbound second probe;

(j) adding said triggering solution to trigger said chemical label; and (k) detecting signals generated by said chemical label on said test snare and said control snare for determining the presence of said second target nucleic acid fragment and said second positive control DNA sequence.

12. The method of claim 11, wherein said target nucleic acid fragments comprise DNA, RNA or PNA.

13. The method of claim 1, wherein said target nucleic acid fragments comprise DNA, RNA or PNA.

* * * * *